United States Patent [19]

Tregoning

[11] 4,319,568
[45] Mar. 16, 1982

[54] LIQUID DISPENSING APPARATUS

[75] Inventor: John A. Tregoning, Reading, England

[73] Assignee: Vickers Limited, London, England

[21] Appl. No.: 88,812

[22] Filed: Oct. 29, 1979

[51] Int. Cl.³ .............................................. A61M 5/00
[52] U.S. Cl. ................. 128/214 F; 417/477; 222/64; 222/255
[58] Field of Search ....................... 222/23, 40, 56, 59, 222/63, 64–68, 207, 450, 255, 333, 420; 417/474, 477, 540, 542; 128/214 C, 214 E, 214 F, 215

[56] References Cited

U.S. PATENT DOCUMENTS

| | | | |
|---|---|---|---|
| 3,224,638 | 12/1965 | Harrell | 222/64 |
| 3,469,574 | 9/1969 | Durkan | 222/64 |
| 3,609,379 | 9/1971 | Hildebrandt | 128/214 E |
| 3,881,640 | 5/1975 | Noble | 222/450 |
| 4,086,924 | 5/1978 | Latham | 128/214 E |
| 4,199,307 | 4/1980 | Jassawalla | 128/214 F |

FOREIGN PATENT DOCUMENTS

| | | | |
|---|---|---|---|
| 2007089 | 10/1971 | Fed. Rep. of Germany | 222/67 |
| 1253283 | 11/1971 | United Kingdom | 222/64 |

*Primary Examiner*—H. Grant Skaggs
*Attorney, Agent, or Firm*—Larson and Taylor

[57] ABSTRACT

Liquid dispensing apparatus comprises a T-tube (9) of which the limb tube serves as a closed reservoir (8) for liquid, with an air space above. Liquid is pumped by a peristaltic pump (A) through a tube (6) and one arm of the T-tube into the reservoir until a level detector (D) responds to the liquid level in the reservoir reaching a datum level whereupon it renders the pump (A) inoperative. A further peristaltic pump (B) then starts to pump liquid from the reservoir out of the other arm of the T-tube and through tubes 13 and 15 to an infusion needle in a patient's body. When the liquid level in the reservoir reaches a predeterined lower level detected by another detector (E), the second pump (B) is rendered inoperative and the cycle is then repeated starting with operation of the first pump (A).

The use of a peristaltic pump as the second pump (B) enables the liquid delivery pressure at the needle to be held just above the minimum necessary for infusion. Also, any air bubbles in the reservoir will generally migrate to the air space. Conveniently, the tube assembly comprising the parts 6, 9, and 13 constitutes a disposable assembly which is very cheap to manufacture.

8 Claims, 4 Drawing Figures

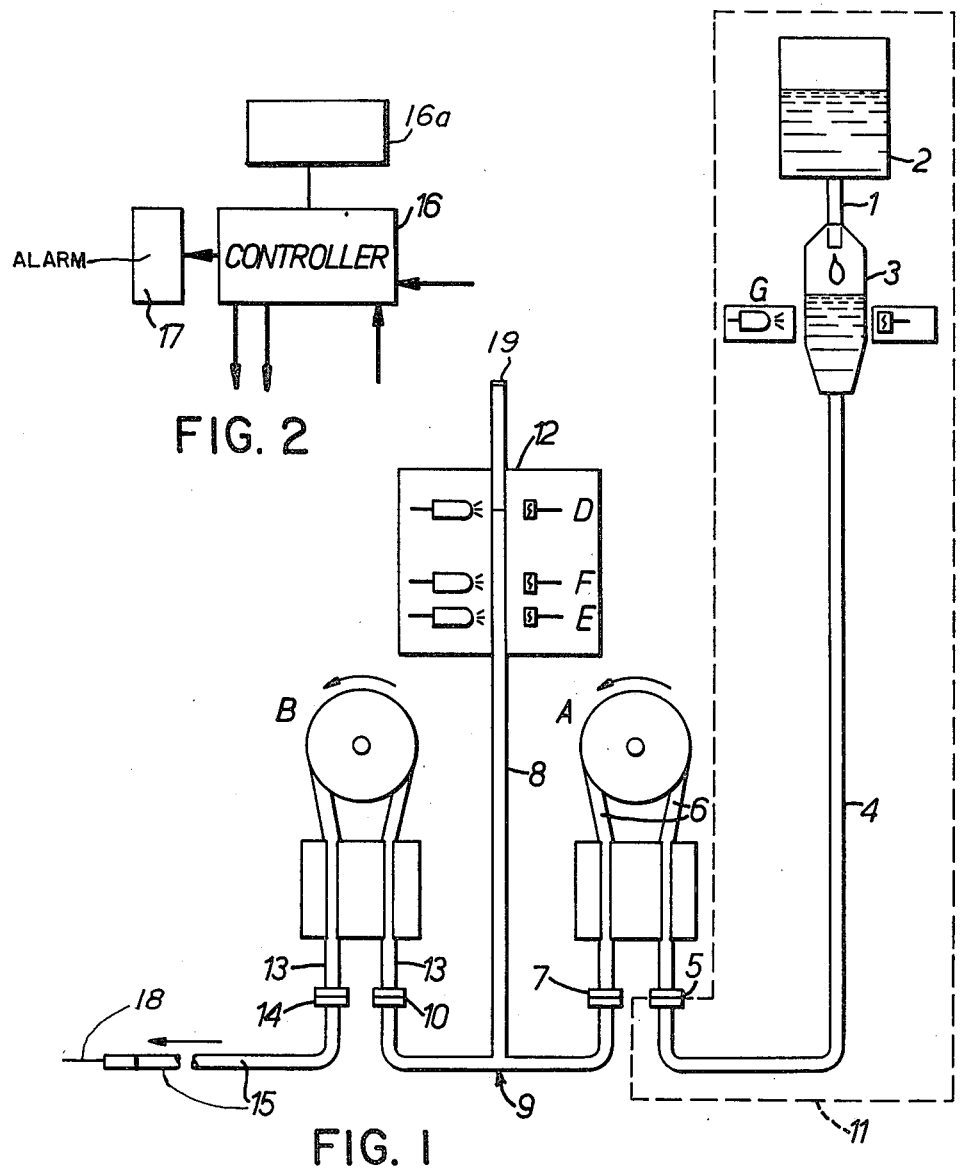

LIQUID DISPENSING APPARATUS

This invention concerns improvements in and relating to liquid dispensing apparatus, in particular though not exclusively medical or veterinary infusion apparatus.

Infusion apparatus for infusing liquids such as glucose, saline solution or drugs, into patients is widely used. In one method of controlling infusion, the rate of production of drips in a drip forming chamber which is connected between the liquid storage bottle of the drip set and an infusion needle inserted into the patient, is maintained at a constant value, using for example a roller clamp on the drip line. In controlling the infusion rate in this way, it is assumed that the volume of each drip is constant. However, factors such as temperature variations, changes in viscosity of the liquid, hydrostatic pressure variations, and pressure variations during infusion can affect the volume of each drip. Whilst these effects in many cases are unimportant, such as when infusing glucose or saline solution, this drip volume variation can in certain circumstances prove unsatisfactory, especially where administering drugs which are particularly potent or expensive. Thus, in some instances it is necessary to effect volumetric control. For this purpose, one standard piece of equipment comprises a storage reservoir with administration set, and a cam-operated reciprocating syringe provided with non-return valves in the supply and outlet/delivery lines, the infusion rate on the delivery stroke of the syringe plunger being controlled by the gradual displacement of the plunger. The syringe with the non-return valves is made as a disposable injection-moulded cartridge. Over a period of use, the cost of the cartridges needed becomes quite considerable. Moreover, the infusion pressure is generally significantly higher than the minimum pressure required for infusion into the patient, and this can be undesirable. Additionally, it can be difficult to prime the syringe and this can result in air becoming trapped in the syringe. To avoid pumping air into the patient with possibly fatal consequences, an air bubble detector is used to monitor the liquid dispensed through the delivery line to the patient, the detector switching off the equipment in the event of an air bubble being detected in the delivery line. This all adds to the cost and complexity of the equipment.

The invention seeks to provide an improvement in the above respects.

According to the invention from one aspect there is provided apparatus for dispensing a predetermined quantity of liquid, comprising a reservoir for liquid, means operative to admit liquid to the reservoir to a predetermined datum level, and dispensing means including a positive displacement peristaltic pump, operative to pump liquid out of the reservoir until the liquid level therein falls from said datum level to a predetermined lower level. The change in level corresponds to the said predetermined quantity of liquid.

This apparatus provides an especially convenient way of delivering a predetermined quantity of liquid. Furthermore, when used as part of infusion equipment, because of the operating properties of peristaltic pumps, the pump pressure can easily be set just above the minimum infusion pressure necessary.

Preferably, control means are provided for controlling operation of the liquid admitting means and dispensing means cyclically so as to deliver a predetermined quantity of liquid at regular intervals. The liquid admitting means preferably also includes a positive displacement pump which may be a peristaltic pump.

According to the invention from a second aspect, there is provided apparatus for dispensing a predetermined quantity of liquid, comprising a reservoir which is closed to provide, in use, an air space above liquid in the reservoir, means operative to admit liquid to the reservoir, a first level detector arranged to render the liquid admitting means inoperative once liquid in the reservoir has risen to a predetermined datum level, means operative to dispense liquid from the reservoir, and a second level detector arranged to render the liquid dispensing means inoperative when liquid in the reservoir has fallen from said datum level to a predetermined lower level.

Again, the change in levels corresponds to the said predetermined quantity of liquid. Any air admitted with the liquid into the reservoir is released into the air space but there is no risk of any of this air being dispensed from the reservoir into the patient because of the function of the second level detector.

The liquid admitting means and dispensing means could both include valves, providing the liquid supply pressure to the admitting means is adequate. When the apparatus forms part of infusion equipment, however, the liquid dispensing means, and possibly admitting means too, preferably includes a peristaltic pump.

The reservoir could be provided with a filter serving as pressure relief means to relieve excess pressure in the air space while preventing entry of any contaminants into the reservoir.

According to the invention from a third aspect there is provided a tube assembly for use in infusion apparatus, comprising a T tube of which the limb tube constitutes a reservoir for liquid and is closed at its free end to provide, in use, an air space above liquid in the reservoir, a first tube connected to one arm tube of the T tube for conveying to the reservoir liquid to be infused, and a second tube connected at one end to the other arm of the T tube and at the other end to a third tube for conveying liquid from the reservoir to an infusion needle, the first and second tubes each being made of material which can be resiliently deformed to close at least partially the passage within the tube. The first and second tubes are intended to be installed as the pumping tubes of respective peristaltic positive displacement pumps so that the operative movable parts (e.g. rollers or fingers) are arranged to exert a pumping action on liquid in the first and second tubes. Alternatively, however, if an adequate liquid supply pressure exists to the first tube, the first and second tubes can be provided with respective clamps so as to control selectively the flow through these tubes.

Such a tube assembly can be made extremely cheap to produce and therefore even over a lengthy period of time involving the use of a large number of fresh tube assemblies, the total outlay is relatively low.

The liquid tube can be closed with a filter serving as pressure relief means for relieving excess pressure from the air space while preventing entry of any contaminants into the reservoir.

For a better understanding of the invention and to show how the same may be carried into effect, reference will now be made, by way of example, to the accompanying drawing wherein FIG. 1 shows diagrammatically one form of liquid dispensing apparatus supplied from an infusion drip set;

FIG. 2 is a block form representation of a controller which can be used to control the operating sequence of the apparatus;

Figure 3:
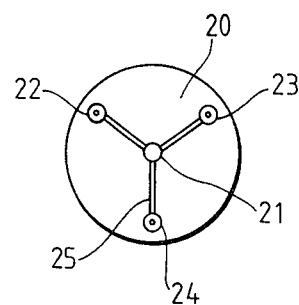
FIG. 3 is a diagrammatic representation of the drive head of a three fingered peristaltic pump.

Referring to FIG. 1, liquid to be infused into a patient can pass through an outlet pipe 1 from a storage bottle 2 and be formed at the lower end of the pipe in an airtight drip forming chamber 3 into droplets. From this chamber, liquid can be pumped by a positive displacement pump A, which is preferably a peristaltic pump, via a pipe 4 of polyvinylchloride for example, a connector 5, a tube 6 and a connector 7, into a reservoir 8 provided by a closed-ended limb tube of a T tube 9 whose arm tubes are respectively connected to the connector 7 and a further connector 10. The limb tube forming reservoir 8 is closed-ended to prevent entry of any contaminants into the reservoir. The parts 1 to 5 constitute a standard drip set 11. It will of course be appreciated that any other suitable form of storage reservoir and administration set could be used in place of the drip set 11 which is illustrated merely by way of example. The reservoir 8 extends through a block 12 including liquid level sensing detectors, D, E, F, which can be optical detectors operating in the infrared region. The purpose of these detectors will be described below. Liquid can be pumped from the reservoir 8 by a positive displacement pump B, which is preferably a peristaltic pump, via a tube 13, a connector 14 and a tube 15, again of polyvinylchloride for example, to an infusion needle 18 inserted into the patient.

The tubes 6 and 13 are each made of material which can be resiliently deformed to close at least partially the passage within the tube. A particularly suitable material is silicone rubber tube. Where the pumps A, B are roller pumps, the tubes 6 and 13 are placed around the rollers so that when each pump rotor rotates, the rollers exert a pumping action on liquid in the tube. Alternatively, the pumps could be three-(or more) finger peristaltic pumps. The pumps can operate at the same or different pressures.

FIG. 3 shows diagrammatically the drive head of a three-finger peristaltic pump. The pump comprises a plate 20 through which passes a drive spindle 21 which supports three pump rollers 22, 23 and 24 on supports or fingers such as that shown at 25.

In use, the liquid system is primed and then the tubes 6, 13 placed around the pump rollers. With pump B at rest, pump A is started to pump liquid into the reservoir 8, compressing air in the reservoir above the liquid, until the liquid rises to the level of detector D. Pump A then stops and pump B starts to dispense liquid from the reservoir into the patient via the tube 15. When the liquid level has fallen to the level of detector E, pump B stops and pump A starts again. This operating cycle is then repeated continuously.

By way of example, for a dispensed flow rate of 60 ml./hr and if the difference in level between the detectors D and E represents a dispensed volume of 1 ml, the cycle operating time is 1 minute. Clearly, it would be desirable for the volume of liquid dispensed per unit time to be adjustable over a large range and the pumps may be unable to provide sufficient variation. For this purpose the detector F is used. As an example, for a flow operating range of 1 ml to 240 ml per hour, the time interval occupied by each cycle would range from 15 seconds to 1 hour. The detector F could be provided at a level above detector E to represent a dispensed volume of 0.1 ml. Then, infusion rates of 10 mls and below could be infused at 0.1 ml volumes per time interval. Then, the longest time interval would be 6 minutes instead of 1 hour. A selector 16a is used to select detector E or F, depending on the range required.

It is pointed out in particular that the tube assembly consisting of the parts 5, 6, 7, 9, 10, 13, 14 and 15 is intended to form a disposable unit which is replaced when required, for example each time a fresh bottle of liquid is to be infused. It will be appreciated that the tube assembly is extremely cheap to produce and this is most advantageous bearing in mind the number of bottles which any given piece of infusion equipment will be required to dispense over any particular period of time.

Figure 4:
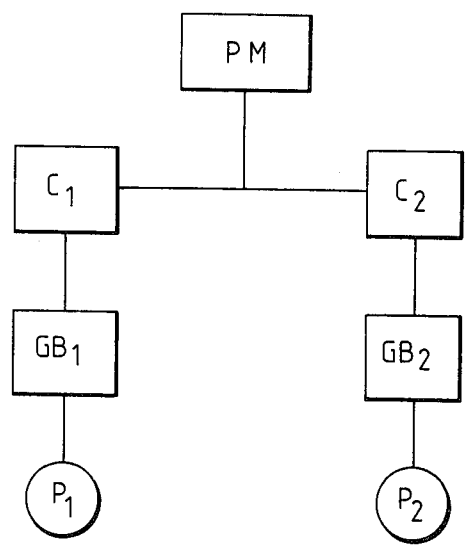
FIG. 4 is a block form representation of the preferred drive arrangement for the two peristaltic pumps in the apparatus.

Expediently, the drive to the two pumps can be provided by a single electric motor operatively coupled respectively by two one-way clutches and two gear boxes to the pumps. This arrangement is illustrated in FIG. 4, which shows a single prime move PM which transmits drive to two one-way clutches $C_1$ and $C_2$. Clutch $C_1$ is connected to gearbox $GB_1$ which in turn is connected to pump $P_1$; similarly, the second clutch $C_2$ is connected to gearbox $GB_2$ which in turn is connected to pump $P_2$. When the motor drives in one direction, one of the clutches slips while the other one transmits drive and vice versa for the opposite direction of motor drive.

As indicated in FIG. 2, a controller 16 can be used to control the entire operating sequence and can be arranged to operate an alarm 17 when certain monitored parameters indicate malfunction. For example, using a detector G, the controller can monitor the level in drip set for the level falling below a minimum value, and/or monitor the time for which detector D is uncovered to determine whether the normal cycle operating time is exceeded and/or monitor the current drawn by the motor per operating cycle and thereby detect the occurrence of the motor-on time exceeding a limit set to just above the time occupied by one complete operating cycle. Other safety factors include limiting the delivery pressure of each pump. In a development, the controller can serve to operate the selector for the detectors D,F automatically, in dependence upon the magnitude of a desired delivery rate set in the controller.

In addition to the cheapness of the disposable tube assembly, the described dispensing apparatus is especially advantageous in that when using peristaltic pump B, the infusion pressure into the patient can very easily be set to just above the minimum pressure required for infusion merely by adjusting the tube tension over the pump rollers. Furthermore, any air admitted to the reservoir 8 will rise to the air space but no air can possibly be pumped from the air space into the patient because the detector E switches off the pump B as soon as the liquid in the reservoir has fallen to the level of that detector.

It should also be noted that if too much air enters the air space, the pump A will be unable to raise the liquid level to that of the detector monitoring the upper level. This in turn prevents pump B from operating. The closed end of the limb tube of the T-tube can be provided with a filter 19 serving as a pressure relief valve to relieve excess pressure from the air space while preventing entry of any contaminants into the reservoir. In one form, the filter can incorporate sintered metal as the filter material.

I claim:

1. Apparatus for dispensing a predetermined quantity of liquid for infusion into a patient, which apparatus comprises a T-tube having a first arm, a second arm and a limb tube, of which the limb tube constitutes a reservoir for liquid and is closed at its free end to provide, in use, an air space above liquid in the reservoir;

a first tube connected at one of its ends to said first arm of the T-tube and made of resiliently deformable material to enable the passage within said first tube to be closed at least partially, the other of the ends of said first tube being adapted for connection to a drip set containing the liquid which is to be infused into the patient;

a second tube made of a material having the same deformation property as said first tube and connected at one of its ends to said second arm of the T-tube and the other of its ends being adapted for connection to an infusion needle;

a first peristaltic pump operative to exert a pumping action on said first tube;

a first level detector external of and adjacent to said reservoir, and arranged to render said first peristaltic pump inoperative once liquid has been pumped into the reservoir to a predetermined datum level;

a second peristaltic pump operative to exert a pumping action on said second tube;

a second level detector external of and adjacent to said reservoir, and arranged to render said second peristaltic pump inoperative when liquid in the reservoir has fallen from said datum level to a predetermined lower level; and control means arranged to control operation of said first and second peristaltic pumps cyclically such that, when said first tube is connected to said drip set and said second tube is connected to said infusion needle, operation of said first pump causes liquid from the drip set to be pumped through said first tube and into said reservoir until the level of liquid reaches said predetermined datum level whereupon said first level detector actuates the control means to render said first peristaltic pump inoperative and simultaneously to commence operation of said second peristaltic pump; and operation of said second peristaltic pump causes liquid to be pumped out of the reservoir through said second tube and thence to the infusion needle until the level of liquid in the reservoir reaches said predetermined lower level, whereupon said second level detector actuates the control means to render said second peristaltic pump inoperative and to restart operation of said first peristaltic pump, whereby a predetermined quantity of liquid is dispensed from the infusion needle at regular intervals.

2. Apparatus according to claim 1, wherein each of the pumps is a three-finger peristaltic pump.

3. Apparatus according to claim 1, wherein the two pumps are provided with a common drive arrangement which comprises a single, reversible-drive, prime mover coupled to each pump through a respective gear box and a respective clutch, the clutches being so arranged that for one of the two directions in which the prime mover can drive, one of the clutches transmits drive while the other one is disengaged, and for the other direction of the drive, the other clutch transmits drive and the one clutch is disengaged.

4. Apparatus according to claim 1, wherein the reservoir is provided with a filter serving as pressure relief means to relieve excess pressure in the air space while preventing entry of any contaminants into the reservoir.

5. Apparatus according to claim 4, wherein the filter incorporates sintered metal as the filter material.

6. Apparatus according to claim 1, wherein a third level detector is positioned at a level between that of the first and second detectors, and selector means are provided operable to select one or other of said first and third detectors for rendering said first peristaltic pump inoperative once liquid in the reservoir has risen to the predetermined datum level associated with the detector concerned.

7. Apparatus according to claim 1, wherein each detector is an optical detector which is responsive in the infra-red region.

8. Apparatus according to claim 1, wherein said control means is responsive to the output value of an additional level detector positioned to monitor the liquid level in a drip forming chamber which forms part of said drip set, so as to provide an output indication in the event of the level of liquid in said drip forming chamber falling below a predetermined minimum level.

* * * * *